United States Patent [19]

Martinoli et al.

[11] Patent Number: 5,072,610
[45] Date of Patent: Dec. 17, 1991

[54] DEVICE FOR MEASURING THE MODIFICATION TIME OF THE PHYSICAL STATE OF A FLUID MEDIUM

[75] Inventors: Jean-Luc Martinoli, Villeneuve La Garenne; Alain Rousseau, Paris; Pascal Vilain, Hadancourt le Haut Clocher, all of France

[73] Assignee: Servio, France

[21] Appl. No.: 679,124

[22] Filed: Mar. 27, 1991

Related U.S. Application Data

[63] Continuation of Ser. No. 291,824, Dec. 29, 1988, abandoned.

[30] Foreign Application Priority Data

Dec. 30, 1987 [FR] France ................. 87 18347

[51] Int. Cl.⁵ .............. G01N 21/82; G01N 27/83
[52] U.S. Cl. ..................... 73/64.1; 422/72; 422/73; 356/39; 366/273; 366/274; 435/13; 436/69
[58] Field of Search ............. 435/13; 436/69; 422/72, 422/73; 73/64.1; 366/273, 274; 356/39

[56] References Cited

U.S. PATENT DOCUMENTS

| 4,612,801 | 9/1986 | Girulami .................. 73/64.1 |
| 4,918,984 | 4/1990 | Marlinoli ................. 73/64.1 |

FOREIGN PATENT DOCUMENTS

WO90192 5/1983 European Pat. Off. .

Primary Examiner—David L. Lacey
Assistant Examiner—David Redding
Attorney, Agent, or Firm—William A. Drucker

[57] ABSTRACT

A device for the measurement of time at which the physical state of a fluid medium is modified, comprises a vertical cup which contains the fluid and the necessary reagents, and in which a ferromagnetic ball is placed and is driven in rotation by an external magnetic field. The cup has at its lower part an annular travel path for the ball and it comprises a detection device which delivers an electric signal whenever the ball passes in front of it which is associated with a measurement unit determining the variation of the time interval between two consecutive passages of the ball.

5 Claims, 2 Drawing Sheets

DEVICE FOR MEASURING THE MODIFICATION TIME OF THE PHYSICAL STATE OF A FLUID MEDIUM

This application is a continuation of application Ser. No. 07/291,824, filed Dec. 29, 1988 and now abandoned.

BACKGROUND OF THE INVENTION

1. Field of the Invention

The present invention relates to a device for measuring the time of modification of the physical state of a fluid medium and, in particular, measuring the coagulation time of blood, of the kind comprising a vertical cup which contains the fluid such as plasma and the necessary reagents and in which a ferromagnetic ball is placed and is rotated by an external magnetic field.

2. Description of the Prior Art

Such a device is described more particularly in the European patent n° 90 192 in which the ball thus driven moves freely on the flat and horizontal bottom of a cup. When the coagulation of the fluid which is contained in the cup takes place, which fluid is here blood plasma to which reagents have been added, the ball moves over a curve directed towards the inside because, so it seems, of the increase of mechanical resistance opposed by the contents of the cup, and its radial movement is detected by means well known in themselves.

The accuracy of measurements thus made leaves much room for improvement, since the radial movement of a ball towards the center of a cup of very small size is a physical magnitude which is difficult to detect and to evaluate satisfactorily. Furthermore, the reproducibility of such measurements is not good, because, particularly, of the complexity of the phenomena on which they are based.

SUMMARY OF THE INVENTION

Thus, the aim of the present invention is to provide a device for measuring the coagulation time of blood of the above specified kind and which overcomes the drawbacks of known devices and, in particular, which allows measurements to be made whose accuracy, reliability and reproducibility are superior to those obtained up to now with apparatus of this type.

Furthermore, an object of the invention is to provide such a measurement device which is practically automatic and in which human intervention is reduced to a strict minimum, without its cost being prohibitive for all that.

This aim and this object, as well as others which will appear further on, are attained in accordance with the invention through a measurement apparatus of the above specified kind, which is characterized by the fact that its cup has at its lower part an annular travel path for the above specified ball, and it comprises a detection device which delivers an electric signal whenever this ball passes in front of it and is associated with a measurement unit determining the variations of the time interval between two consecutive passages of the ball in question. It will be understood that movement of the ball over a fixed travel path, and no longer haphazardly, on the flat bottom of a cup as in the above European patent n° 90 192 makes high accuracy and good reproducibility of the measurements possible, since it is sufficient to detect variations of the frequency of electric signals, which is an easy operation for specialists in the field.

Such detection is evidently easier and less subject to errors than that which consists in determining the escapement towards the center of the cup of a ball of very small size.

In an advantageous embodiment of the device of the invention, the above specified ferromagnetic ball is driven in rotation by an electric motor whose output shaft is fast with a ferromagnetic rod which is disposed under the cup containing the ball while having the same axis as it, which passes through a coil fed with current and which ends at its upper part in a ferromagnetic finger off-centered with respect to the common axis of this rod and the cup.

This off-centered finger becomes a magnetic pole under the effect of the coil through which the core passes which is fast therewith, and it drives the ball contained in the cup in rotation at an angular speed which is equal to its own as long as the coagulation of the blood has not slowed down the ball in question. This speed may be adjusted, as will be seen further on, which provides different advantages which will be mentioned at the appropriate time.

Advantageously, the device of the invention comprises a first reflex detector of conventional type associated with the rotating ball, a second reflex detector similar to the first one and associated with the off-centered finger which drives the ball, and a comparator connected to a microprocessor for detecting any synchronism defect between the signals delivered by the above two detectors. It is then sufficient to compare the signals from the latter, which are identical with each other, for detecting coagulation of the plasma contained in the cup. Because it is then a question of comparing two signals and not processing a single signal and further because these signals come from two identical detectors, the accuracy of the measurement is increased and its processing by electronic means facilitated.

For rotating the ferromagnetic ball of the invention, and in a variant, the above specified rotary off-centered finger may be replaced by a plurality of fixed poles which surround the cup containing the ball, substantially on the same plane as the latter, and which are magnetized by coils fed with variable currents so as to produce a rotating field in the plane of the ball.

Whatever the method of driving the ball, the measurement device of the invention advantageously comprises means for imparting to the ball a rotational speed and a drive force which are variable as a function of the test carried out and of the duration of the measurement.

In an advantageous embodiment, this rotational speed and this drive force are higher at the beginning of the measurement than at the end with, preferably, a level stretch at the beginning of the measurement and where the speed of the rotation and the drive force of the ball are relatively high, and a level stretch at the end of the measurement where these values are lower, these two level stretches being joined together by a progressive and for example, linear decrease.

This driving law is based on the fact that in hemostasis tests of which it is a question here, clots of very different viscosities are created in time intervals which are also very different, the thick clots appearing at the very beginning and the weak clots at the end. The regulation according to the invention of the rotational speed of the ball and its drive force makes it possible to conciliate good accuracy, of about 0.1 sec for thick clots and high sensitivity for the weaker clots, the accuracy being obtained with a high speed which may be about 10 revolutions per second, and the sensitivity with a reduced drive force and speed, this latter being possibly equal to about 3 revolutions per second.

In the above specified embodiment where the ball is driven by an eccentric rotating finger, such regulation is advantageously obtained because its drive motor is a DC motor and because it is fed, like its magnetization coil through respective regulation means controlled by a microprocessor. Then the speed is very simply regulated by varying the DC voltage at the terminals of the motor and the drive force by adjusting the current flowing through the coil, the law of variation as a function of time of these two values being controlled by the microprocessor.

In an advantageous embodiment, the device of the present invention may also include an optical densitometer comprising a light-emitting diode which is fed from a microprocessor and which illuminates a photodiode through an optical band pass filter, the light beam passing through the cup of the apparatus of the invention above the ball which it contains, and the information from the photodiode being transmitted to the above microprocessor.

Although this densitometer intended for so-called colorimetry measurements is independent of the mechanical coagulometer which has just been described, the association of these two apparatus in the same unit appreciably simplifies a number of operations. It further makes it possible to reduce the cost, because different associated members are used for two different purposes such as the temperature regulation devices, the power supplies and/or part at least of the man/machine interfaces, these elements being further possibly common to several measurement cups housed in the same apparatus. Moreover, the ball of the mechanical coagulometer may also serve as agitator for the densitometer.

BRIEF DESCRIPTION OF THE DRAWINGS

The following description, which has no limitative character will better show how the present invention may be put into practice. It should be read with reference to the accompanying drawings in which.

DESCRIPTION OF THE PREFERRED EMBODIMENT

Figure 1:
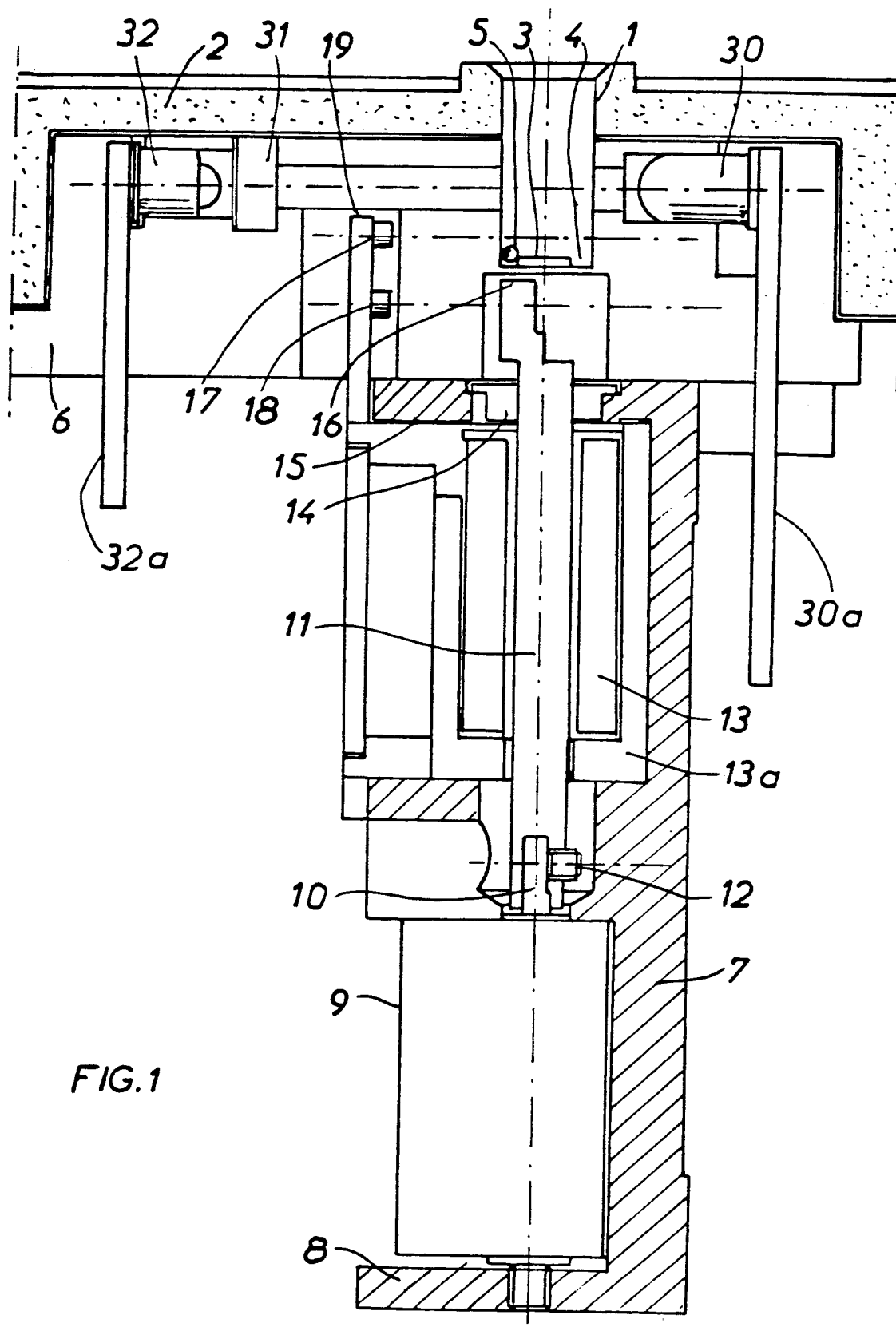
FIG. 1 shows a schematic axial sectional view of the measurement device of the invention.

In the embodiment shown in FIG. 1, the measurement apparatus of the invention comprises a cylindrical cup 1 which is inserted vertically with an easy fit in an upper plate 2 and whose bottom comprises a central stud 3, which defines between the latter and the wall of the cup 1 an annular travel path 4 for a ball 5 made from a ferromagnetic material which is generally steel.

In the lower part of plate 1 a measurement block 6 is screwed which is fixed to a lower frame 7 on the horizontal base 8 of which a DC electric motor 9 is mounted whose shaft 10 is vertical, directed upwardly and coaxial with the cup 1 A soft iron core 11 caps, at its lower end, the shaft 10 of motor 9 with which it is coaxial and on which it is fixed by a screw 12. This core 11 passes through a vertical coil 13 connected to a DC current source not shown and surrounded by a magnetic screen 13a. Core 11 then passes through a guide bearing 14 mounted in the upper part 15 of frame 7, above which it projects by a finger 16 off TM centered with respect to the common axis of the cup 1, motor 9 and core 11.

A first reflex detector 17, of known type, is mounted outside cup 1, but in the immediate vicinity thereof, its axis being horizontal and situated substantially at the level of ball 5. A second reflex detector 18, similar to the first one, is mounted at the height of the off-centered finger 16 which is mounted over the rotating core 11, and its axis is also horizontal. These detectors 17 and 18 are advantageously mounted on a printed circuit board 19 which is in its turn fixed to frame 7.

It will be understood that the supply of DC electric current to coil 13 magnetizes the rotating core 11 which passes through it and this transforms the off-centered finger 16 thereof into a magnetic pole which, in its turn, causes ball 5 to rotate along its annular travel path 4.

Figure 2:
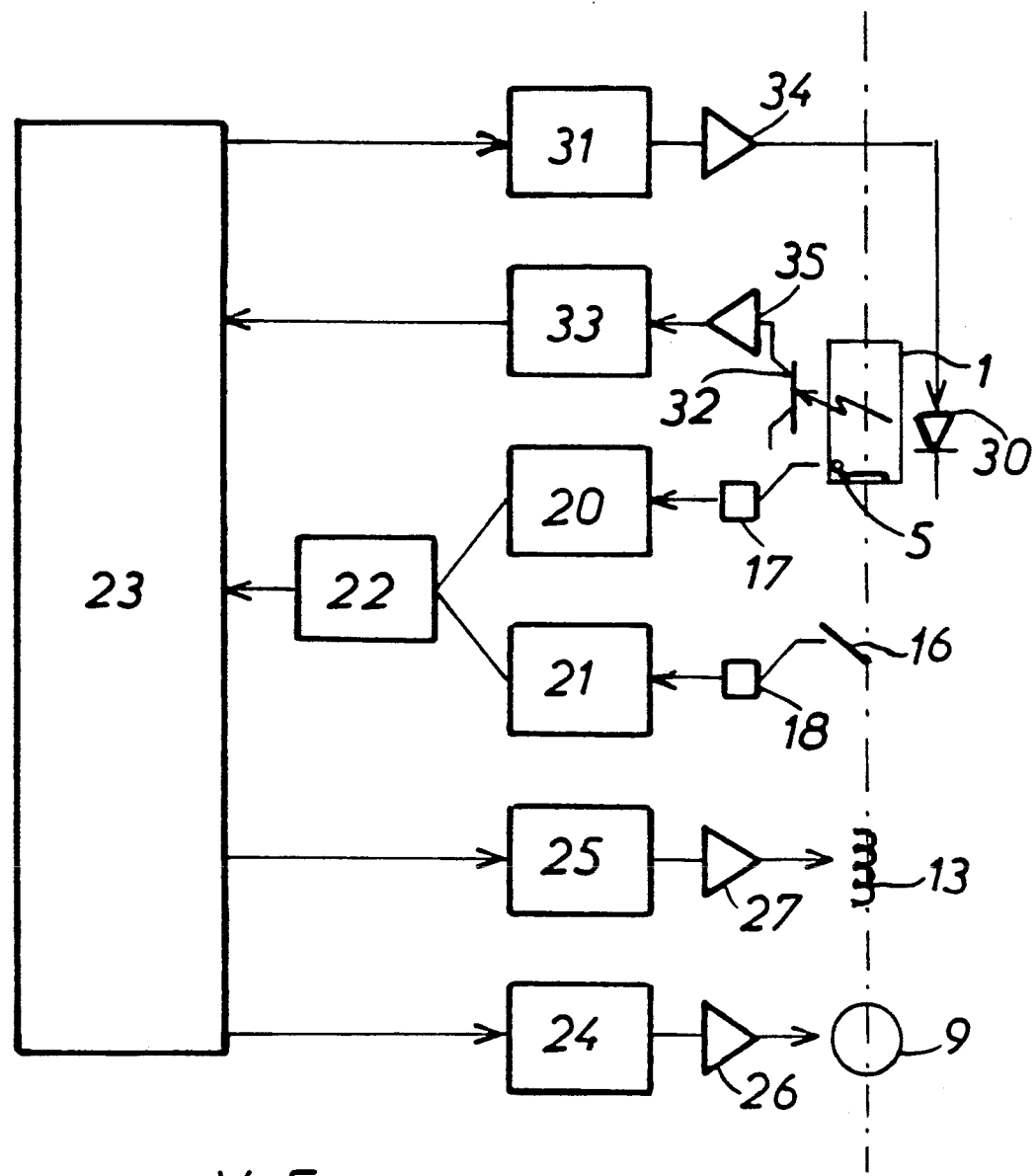
FIG. 2 shows a schematic diagram which represents the main electric circuits of the device.

When plasma has been poured into cup 1 so as to cover ball 5, this latter rotates in synchronism with the off-centered finger and the electric signals delivered by the two detectors 17 and 18 coincide exactly in time. On the other hand, when the plasma begins to coagulate in cup 1 following the introduction of appropriate reagents, ball 5 slows down and the signals from detector 17 associated with ball 5, on the one hand, and those from detector 18 corresponding to the drive finger 16, on the other, begin to be offset with respect to each other. This information is detected and used by the electronic device of FIG. 2.

In the diagram of this figure, we find again the ball 5 rotated in cup 1 by the off-centered finger 16 under the influence of motor 9 and coil 13, as well as the detectors 17 and 18 associated respectively with ball 5 and the rotating finger 16.

The sensors 17 and 18 are connected by filtering cells 20 and 21 respectively, to a comparator counter 22 whose information supplies a microprocessor 23. The latter also controls the DC supply to motor 9 and coil 13 through regulators 24, 25 respectively and respective amplifiers 26 and 27.

Thus, the comparator 22 detects the slowing down of ball 5 when the plasma begins to coagulate. The microprocessor Z3 which is associated therewith uses this information, for example by displaying the value of the coagulation time, by printing it, storing it etc. Such operations are well known to specialists in the field, as well as the devices required for conducting them correctly, and they will not be described in greater detail here.

Furthermore, and as was mentioned above, it is advantageous to impose a driving law as a function of time on the speed of rotation and the drive force of ball 5, which takes place by regulating the voltage at the terminals of motor 9 and, respectively, the intensity of the current which flows through coil 13. The value of these electric magnitudes at each moment is imposed by the microprocessor 23 through the regulators 24, 25 and the amplifiers 26, 27.

Figure 3:
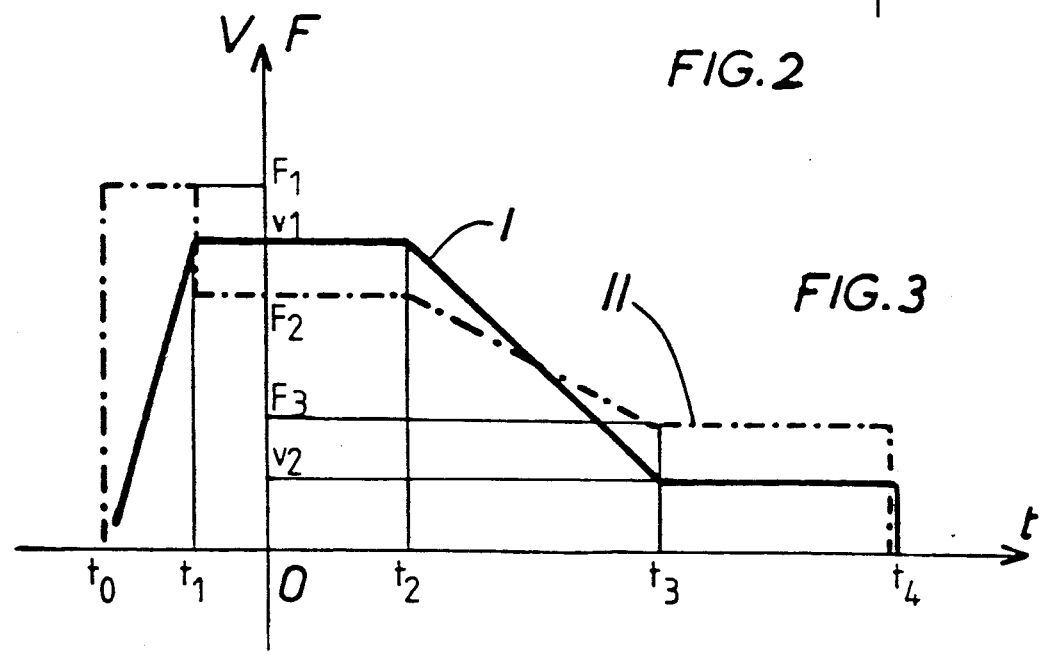
FIG. 3 shows two curves which represent the driving law of this device as a function of time.

This driving law may be represented by the curves of FIG. 3 which show, as a function of time t in seconds, the variations of the rotational speed V of motor 9, and so of ball 5, for curve I, and that of the drive force F for this same ball 5 for curve II.

As can be seen in this figure, starting from the start-up time $t_0$ and until time $t_1$, slightly less than the beginning of the test which corresponds to the origin 0 of the coordinates, the speed increases linearly up to a value $V_1$ which may be equal to 10 revs/s whereas the drive force remains equal to a relatively high value $F_1$. The speed then remains constant up to a time $t_2$ subsequent, by 10 seconds for example, to the beginning 0 of the test, whereas the force also remains constant, but after having taken on a new value $F_2$ less than the preceding one. The two values in question then decrease linearly to a time $t_3$ which may be equal to 60 seconds—reckoned of course from the beginning 0 of the test—and remain constant until time $t_4$ at the end of the test. This second level stretch corresponds to a speed $V_2$ which may be equal to about 3 revs/s and to a force equal to about half $F_2$.

As was explained above: this drive law makes it possible to obtain a high precision, of about 0.1 second, at the beginning of the measurement and a good sensitivity at the end. The device of the invention makes it then possible to detect thick clots, then weak ones, because of a progressive controlled variation in time of the parameters of the system.

Returning to FIG. 1, it will be further noted that the device of the present invention may further comprise an optical densitometer for making so-called colorimetry measurements, mounted on the measurement block 6 which also serves as support for the mechanical coagulometer described above.

This densitometer essentially comprises a light source formed by a LED 30, a bypass optical filter 31 and an optical receiver formed by a photodiode 32 followed by an electronic filter. Diode 30 is mounted on a printed circuit board 30a fixed to the measurement block 6, whereas filter 31 and photodiode 32 are fixed to another printed circuit board 32a also fixed to the measurement block 6. These elements can be found again, shown schematically, in FIG. 2 to which reference will now be made and in which the electronic filter of the photodiode 32 is designated by the reference 33.

In a particular embodiment given by way of non limitative example, the LED 30, whose maximum light intensity is about 480 nm, is fed from the microprocessor 23 by a regulated current chopped at a few kilohertz, through the filter 31 which transmits the light up to about 500 nm. This diode 30 illuminates the photodiode 32 with which it is placed in line, so that the light beam passes through the plasma and cup 1 in a horizontal plane above ball 5. The information delivered by the photodiode 32 is transmitted to the microprocessor 23 through a filter 33 which allows only the chopped signal from source 30 to be held back. Finally, amplifiers 34 and 35 are inserted respectively between filters 31, 33 and diodes 30, 32.

What is claimed is:

1. A device for measuring the time of change of the physical state of a fluid sample comprising:
   a container for holding the fluid sample;
   a ferromagnetic member positioned and arranged so as to be movable in the bottom of the container along a predetermined circular path;
   a driving means for generating a periodic rotating magnetic field to said ferromagnetic member which imparts to said member a sustained circular motion along said path; and
   a detecting means for detecting the variations of frequency of said circular motion of said ferromagnetic member during the time of change in the physical state of the fluid sample, said detecting means further comprising means for measuring the relative speed of said sustained circular motion of said ferromagnetic member and the relative speed of said periodic rotating magnetic field during the time of change of the physical state of the sample fluid,
   and means for comparing said measured relative speeds to provide the time of change of physical state of the sample fluid.

2. A device as claimed in claim 1, wherein said container is a vertically arranged cylinder having an axis of symmetry and a bottom provided with said circular path centered on said axis of symmetry, said driving means comprise a generally cylindrical ferromagnetic core vertically arranged under said cylinder and coaxial therewith, said core having an upper projection having a surface portion facing said ferromagnetic member, said driving means further comprising motor means drivingly coupled to said core for rotating it about said axis and means for magnetizing said core, and said measuring means comprise means for detecting the respective passage of said ferromagnetic member and of said surface portion of said core in a predetermined angular position and means for measuring the time interval between the said respective passages.

3. The device as claimed in claim 1, wherein said driving means include means for imparting to said ferromagnetic member a rotational speed and a drive force which have variable values as a function of the test carried out and of the duration of the measurement.

4. The device as claimed in claim 3, wherein said means for imparting a variable speed of rotation and a variable drive force are such that said values have at the beginning and at the end of the measurement first and second respective level stretches, the values corresponding to the first stretch being higher than those corresponding to the second stretch and gradually decreasing from the first to the second stretch.

5. The device of claim 1 further comprising an optical densitomer which comprises:
   an optical filter; and
   a light source in the form of a LED fed from a microprocessor, said microprocessor electrically connected to said LED and a photodiode;
   whereby a light beam produced by said LED is transmitted from said microprocessor, through said container and said optical filter to the photodiode.

* * * * *